(12) United States Patent
Gao et al.

(10) Patent No.: US 12,060,300 B2
(45) Date of Patent: Aug. 13, 2024

(54) METHOD FOR CALCULATING GASEOUS DIFFUSION AND OXIDATION EVOLUTION OF CERAMIC MATRIX COMPOSITE (CMC) STRUCTURE

(71) Applicant: Nanjing University of Aeronautics and Astronautics, Nanjing (CN)

(72) Inventors: Xiguang Gao, Nanjing (CN); Yingdong Song, Nanjing (CN); Guoqiang Yu, Nanjing (CN); Sheng Zhang, Nanjing (CN); Xiaoting Shi, Nanjing (CN); Zheng Ni, Nanjing (CN)

(73) Assignee: Nanjing University of Aeronautics and Astronautics (CN)

( * ) Notice: Subject to any disclaimer, the term of this patent is extended or adjusted under 35 U.S.C. 154(b) by 284 days.

(21) Appl. No.: 17/586,384

(22) Filed: Jan. 27, 2022

(65) Prior Publication Data
US 2023/0234890 A1    Jul. 27, 2023

(51) Int. Cl.
G01N 33/38 (2006.01)
C03C 10/00 (2006.01)
C04B 35/52 (2006.01)
C04B 35/80 (2006.01)

(52) U.S. Cl.
CPC ......... C04B 35/52 (2013.01); C03C 10/0036 (2013.01); C04B 35/80 (2013.01); G01N 33/388 (2013.01); C03C 2214/20 (2013.01)

(58) Field of Classification Search
CPC ..... C04B 35/52; C04B 35/80; C03C 10/0036; C03C 2214/20; G01N 2223/615; G01N 23/046; G01N 33/388

USPC ............. 374/45–52; 378/21–27; 702/33–35; 73/38, 86, 788, 799, 865.8, 865.9, 866, 73/866.4

See application file for complete search history.

(56) References Cited

FOREIGN PATENT DOCUMENTS

| | | | | |
|---|---|---|---|---|
| CN | 108359971 A | * | 8/2018 | |
| CN | 110246548 A | * | 9/2019 | |
| CN | 113321510 A | * | 8/2021 | ......... C04B 35/5607 |

* cited by examiner

*Primary Examiner* — Robert R Raevis
(74) *Attorney, Agent, or Firm* — The Farrell Law Firm, P.C.

(57) ABSTRACT

A method is provided for calculating gaseous diffusion and oxidation evolution of a ceramic matrix composite (CMC) structure, which includes determining temperature and load distribution in a structural member; determining matrix crack distribution in the structure; establishing an equivalent diffusion coefficient model of a fiber bundle scale to predict a gas flow channel in a fiber bundle: averaging a total amount of gaseous diffusion in the channel to establish the equivalent diffusion coefficient model of the fiber bundle composite scale related to the matrix crack distribution; establishing a representative volume element (RVE) model; establishing an equivalent diffusion coefficient model of a RVE scale; calculating the distribution of the gas concentration and oxidation products in the structure; calculating a growth thickness of an oxide at cracks and pores in each element; and updating sealing conditions of the gas channel, and calculating a new equivalent diffusion coefficient field and the distribution of the oxidation products again.

7 Claims, 4 Drawing Sheets

METHOD FOR CALCULATING GASEOUS DIFFUSION AND OXIDATION EVOLUTION OF CERAMIC MATRIX COMPOSITE (CMC) STRUCTURE

BACKGROUND

1. Field

The present disclosure relates generally to oxidation analysis of ceramic matrix composites (CMCs), and more particularly, to a method for calculating oxidation evolution and distribution of a gas concentration considering an uneven distribution of oxidation products.

2. Description of Related Art

CMCs have extensive application prospects in the field of aero-engine hot-end components due to their excellent mechanical properties at high temperatures. In the service process, a CMC structural member is subjected to a coupling effect of high temperature, stress, and oxidation, resulting in the reduction of structural strength. Realizing the oxidation calculation of a CMC structure in a high temperature environment, and obtaining the morphology after oxidation can provide initial parameters for a calculation of remaining mechanical properties after oxidation, which is the basis of strength analysis and life prediction of the CMC structure after oxidation.

In order to reliably apply the CMCs to engineering practice, many scholars around the world have studied the oxidation behavior of the CMCs in a stress oxidation environment. Most of existing methods involve oxidation kinetic analysis at a material level, and the research on the oxidation of the CMCs at a structural level has not been disclosed. For example, a method for predicting internal oxidation morphology of unidirectional CMCs in stress water vapor environment has been taught. Additionally, a method for predicting internal oxidation morphology of unidirectional SiC/SiC composites under a stress oxidation environment has been taught, which takes into account a change of the oxidation notch morphology of a C interface.

This method is based on an oxidation kinetic model in order to calculate oxidation at the CMC level. Environmental parameters (such as temperature, pressure, and gas concentration) of a contact surface of the material and the oxidation environment need to be determined in advance. However, due to the differences in the distribution of internal matrix cracks and pores between fiber bundles in the actual CMC structure, there are oxidizing gas channels of different scales. This phenomenon leads to different gas concentrations at various points in the structure, so the oxidation degree is also different. Based on the existing material-level model, it is difficult to determine the gas concentration at each point inside the structure, so it is difficult to predict the distribution of oxidation products inside the structural member during reaction diffusion. Therefore, it is necessary to provide a method for calculating oxidation of a woven CMC structure to solve the gas distribution problem caused by differences in the diffusion channels and realize the oxidation calculation at the CMC structure level.

SUMMARY

Embodiments of the disclosure provide a method for calculating gaseous diffusion and oxidation evolution of a CMC structure.

According to an aspect, a method is provided for calculating gaseous diffusion and oxidation evolution of a CMC structure. A temperature and a load distribution are determined in a structural member. A matrix crack distribution is determined the CMC structure by, according to a temperature field and a stress field, based on a matrix cracking model, calculating a matrix crack density and a matrix crack width related to a temperature and a stress in the CMC structure. Based on the matrix crack distribution, a total amount of gaseous diffusion in a gas flow channel is averaged to establish an equivalent diffusion coefficient model of a fiber bundle composite scale related to the matrix crack distribution based on the matrix crack width and the matrix crack density in fiber bundle composites with an axial length. A representative volume element (RVE) model of woven CMCs is established by conducting image recognition on an X-ray computed tomography (XCT) scan image of a meso-structure of the woven CMCs used in the structural member, describing a warp direction by a cosine function, describing weft yarns in a form of a straight line, and observing to obtain geometric parameters to establish the RVE model. An equivalent diffusion coefficient model of a RVE scale is established to characterize a gas flow of the CMC structure, by, based on pore characteristics, regarding the fiber bundle as a homogeneous material, and substituting the equivalent diffusion coefficient model of the fiber bundle composite scale into the yarn of the RVE model to establish the equivalent diffusion coefficient model of the woven CMCs on the RVE scale. A distribution of a gas concentration in the CMC structure is calculated by calculating the distribution of the gas concentration of each element in the CMC structure in a transfer direction using a finite difference method. A distribution of oxidation products in the structure is calculated by calculating a growth thickness of an oxide at cracks and pores in each element according to the gas concentration. Sealing conditions are calculated including changes in the crack width and a pore characteristic quantity of the gas channel, a new gas channel characteristic quantity is substituted into the averaging and establishing steps, a new equivalent diffusion coefficient field is calculated to realize recalibration of the gas channel, and calculation of the distribution of the gas concentration and the calculation of the distribution of oxidation products are repeated to realize a calculation of distribution of the oxidation products in the structural member at different times.

The oxidation calculation of a CMC structure takes into account the change of the distribution of the gas concentration caused by the difference in the gas channel inside the structure during reaction diffusion. Based on the diffusion theory of porous media, the equivalent diffusion coefficient models of the fiber bundle composite scale and the woven RVE scale are provided to simulate the oxidation process after reaction-diffusion interaction, which is the basis for the strength analysis and life prediction of the structural member.

The equivalent diffusion coefficient field related to the distribution of the cracks and the pores is established, and the evolution of the gas channels of different scales inside the CMC structure is predicted.

The change of the distribution of the gas concentration inside the structure caused by the channel difference is calculated.

The oxidation evolution and distribution of the gas concentration of the CMC structure level under different working conditions is calculated.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Embodiments are described in detail with reference to the accompanying drawings. The same or similar components may be designated by the same or similar reference numerals although they are illustrated in different drawings. Detailed descriptions of constructions or processes known in the art may be omitted to avoid obscuring the subject matter of the disclosure. The embodiments and the terms used therein are not intended to limit the technology disclosed herein to specific forms, and should be understood to include various modifications, equivalents, and/or alternatives to the corresponding embodiments. A singular expression may include a plural expression unless they are definitely different in a context.

Figure 1:
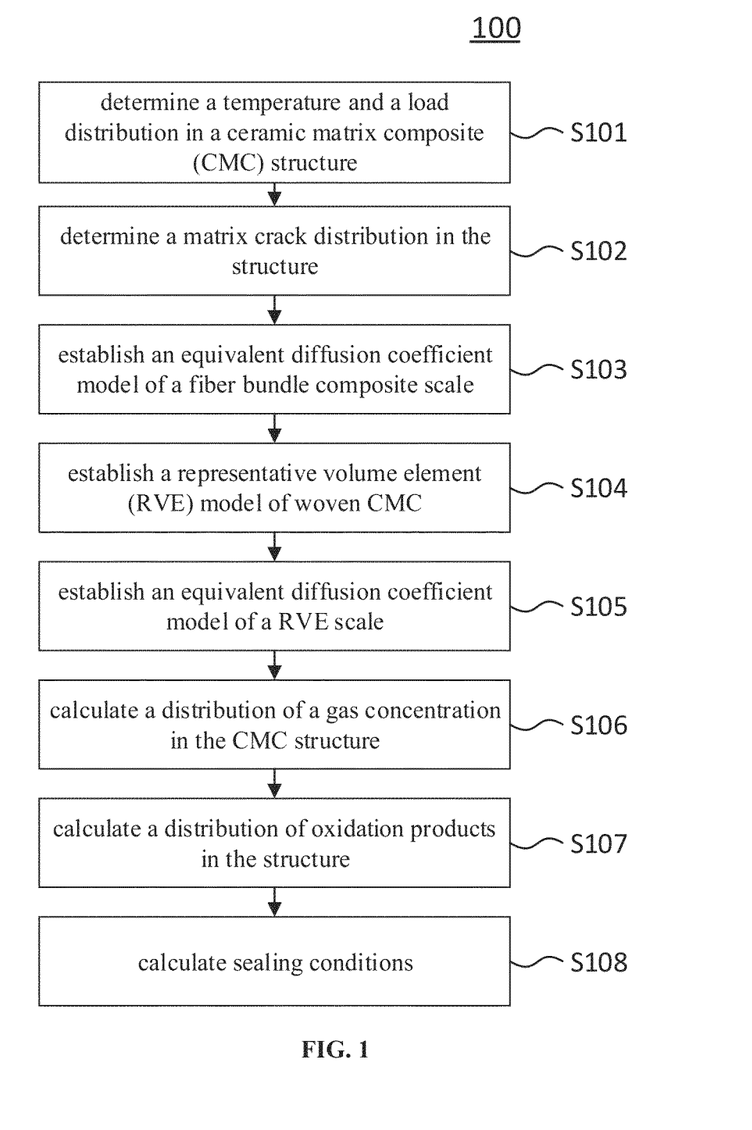
FIG. 1 is a flow chart of oxidation evolution and distribution of a gas concentration of a woven CMC structure, according to an embodiment.

Herein, a method 100 for calculating oxidation of a woven CMC structure is provided by the present disclosure to calculate distribution of oxidation products of a CMC adjustment sheet based on initial conditions of actual working conditions. FIG. 1 is a flow chart illustrating oxidation evolution and distribution of a gas concentration of a woven CMC structure, according to an embodiment.

In step 101, a macroscopic geometric model of the adjustment sheet is established. Linearly varying temperature and pressure loads are applied on an inner side of the adjustment sheet. A constant load is applied on the outer side of the adjustment sheet. Temperature and stress distribution in the adjustment sheet is calculated by a finite element method.

In step 102, matrix crack distribution in the structure is determined. According to a determined temperature field and stress field, and based on a matrix cracking model, a matrix crack density $\rho_{crack}$ and a matrix crack width $d_{crack}$, related to temperature and stress in the structure, are calculated.

The matrix crack density is set forth as Equation (1) below:

$$\rho_{crack} = 1/L = [1 - \exp(-\left(\frac{\sigma}{b_0}\right)^m)]/L_{sat} \quad (1)$$

m and $b_0$ represent a Weibull modulus and a Weibull matrix cracking characteristic strength, respectively. By fitting a transition section of a tensile test curve, m is determined to be equal to 3, and $b_0$ is determined to be equal to 160 MPa. A saturated crack spacing $L_{sat}$ is equal to 357.1 um, and may be observed through a test.

The matrix crack width is set forth as Equation (2) below:

$$\frac{d_{crack}}{d_0} = \frac{1}{T_0}(\frac{1}{E_f V_m (\alpha_m - \alpha_f)}\sigma + \Delta T) \quad (2)$$

In the Equation (2), $d_0$ is a crack width at a normal temperature, $T_0$ is a temperature for material preparation, $\Delta T$ is a temperature difference between a current temperature and the normal temperature, $E_f$ is a fiber elastic modulus, $V_m$ is a volume content of a matrix in the fiber bundle composites, and $\alpha_m$ and $\alpha_f$ are thermal expansion coefficients of the matrix and a fiber, respectively.

Material parameters of SiC/SiC fiber bundle composites are listed in Table 1 below.

TABLE 1

| Material parameters | Value | Material parameters | Value |
|---|---|---|---|
| $E_m$/GPa | 350 | $E_f$/GPa | 146 |
| $V_m$ | 0.675 | $\Delta T$/° C. | −1000 |
| $\alpha_m$/×10$^{-6}$/° C. | 4.6 | $\alpha_f$/×10$^{-6}$/° C. | 3.1 |

In step 103, based on the matrix crack distribution, an equivalent diffusion coefficient model of a fiber bundle scale is established to predict a gas flow channel in a fiber bundle. Based on the matrix crack distribution, a total amount of gaseous diffusion in the channel is averaged to establish the equivalent diffusion coefficient model of the fiber bundle composite scale related to the matrix crack distribution, considering a matrix crack width being $d_{crack}$ and a matrix crack density being $\rho_{crack}$ in fiber bundle composites with an axial length of L, and as set forth in Equation (3) below.

$$D_{mini} = -\frac{N_A}{\frac{dc}{dl}} = \rho_{crack} d_{crack} D_{gas} \quad (3)$$

$N_A$ is a gaseous diffusion flux, $$\frac{dc}{dl}$$

represents a concentration gradient, and $D_{gas}$ is a diffusion coefficient of oxygen in a single crack channel.

Considering that in the range of 0-1,500° C., $O_2$ had a molecular mean free path in the order of $10^{-7}$ m and a crack scale in the order of $10^{-7}$ m, the diffusion belongs to mixed diffusion, the calculation is conducted according to an empirical formula of Fick diffusion (a diffusion coefficient $D_F$) and Knudsen diffusion (a diffusion coefficient $D_K$), as set forth in Equation (4) below:

$$D_{gas}^{-1} = D_F^{-1} + D_K^{-1} \quad (4)$$

Fick diffusion is calculated as set forth in Equation (5) below:

$$D_F = \frac{0.00143 T^{1.75}}{P \overline{M}^{0.5} [(\Sigma_v)_A^{\frac{1}{3}} + (\Sigma_v)_B^{\frac{1}{3}}]^2} \quad (5)$$

Knudsen diffusion is calculated as set forth in Equation 6 below:

$$D_K = \frac{2}{3}\left(\frac{8 R_g T}{\pi M_A}\right)^{0.5} d_{crack} \quad (6)$$

In the equations above, T is an ambient temperature (K), P is ambient pressure (Pa), $R_g$ is a gas constant (J/(mol/K)), $\Sigma_v$ is a molecular diffusion volume, and $\overline{M}$ is a molar mass of mixed gas. In a binary diffusion system ($O_2$—CO), a parameter $\overline{M}$ is calculated as set forth in Equation (7) below (A and B represent $O_2$ and CO respectively).

$$\overline{M} = \frac{2}{M_A^{-1} + M_B^{-1}} \tag{7}$$

$M_A$ = 32 g/mol, $M_A$ = 28 g/mol, $\sum_{vA}$ = 16 cm³/mol, and $\sum_{vB}$ = 18.9 cm³/mol.

The equations above are substituted into the equivalent diffusion coefficient model of the fiber bundle composite scale. A mathematical relationship between an equivalent diffusion coefficient and the matrix crack distribution (crack density and crack width) of the fiber bundle composites is established as Equation (8) below:

$$D_{mini} = \frac{\left(0.00572\sqrt{2}\, R_g^{0.5} T^{1.75} \rho_{crack} d_{crack}^2\right)}{4\sqrt{2}\, P\overline{M}^{0.5}\left[\left(\sum_V\right)_A^{1/3} + \left(\sum_V\right)_B^{1/3}\right]^2 R_g^{0.5} d_{crack} + 0.00429(\pi M_A)^{0.5} T^{1.25}} \tag{8}$$

The equivalent diffusion coefficient of the fiber bundle in each element is calculated by substituting the finite element calculation results of the adjustment sheet.

Figure 2:
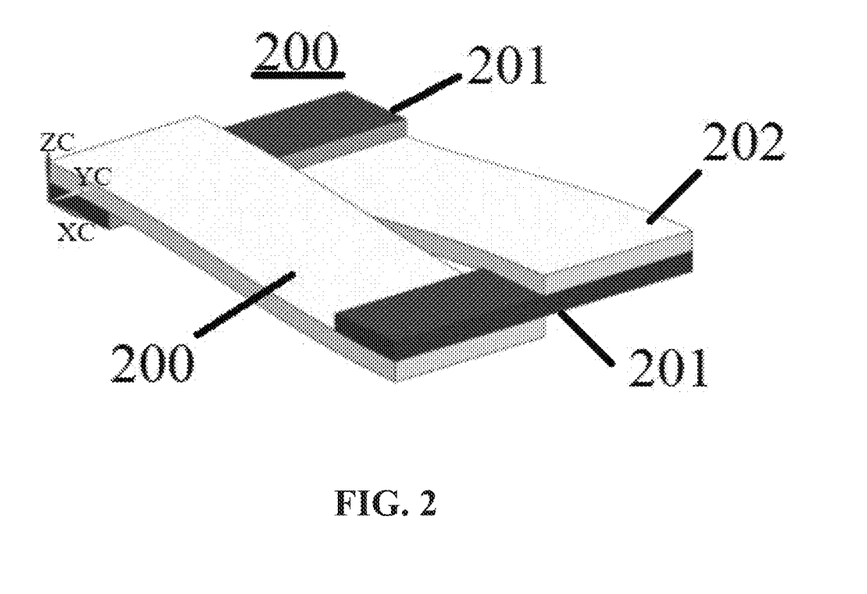
FIG. 2 is an established RVE model of woven CMCs, according to an embodiment.

In step 104, a RVE model 200 is next established, as shown in FIG. 2 that is a diagram illuminating an established RVE model of woven CMCs according to an embodiment. Image recognition is conducted on a meso-structure of the woven CMCs used in the structural member 300 to obtain meso-geometric parameters. A single-layer fiber cloth 201 is selected in a z direction, a part between midlines of two weft yarns is selected in an x direction, and two warp yarns 202 with different winding directions are selected in a y direction to obtain the RVE 200 of the woven CMCs. The fiber bundles in the model (cross-section width 0.94 mm, and height 0.22 mm) are arranged in the same structure as the actual material. A warp direction is described by a cosine function (amplitude 0.22 mm, and wavelength 10 mm), and the weft yarns are distributed in a straight line.

In step 105, an equivalent diffusion coefficient model of a RVE scale is then established. Based on pore characteristics, the yarn is regarded as a homogeneous material, and the equivalent diffusion coefficient model of the fiber bundle composites, previously established, is substituted to establish an equivalent diffusion coefficient model of the woven CMCs on the RVE scale. For the RVE model, a length of any yarn i is assumed to be $L_i$, and a stress value is set as $\sigma_i$. The matrix crack width of the yarn is $\rho_{crack}^i$, and the equivalent diffusion coefficient in the yarn is set forth below as Equation (9):

$$D_{mini}^i = \rho_{crack}^i d_{crack}^i D_{gas}^i \tag{9}$$

An amount of the gaseous diffusion in each yarn crack in the RVE model is set forth below as Equation (10):

$$\frac{dm_1}{dt} = \sum A_i N_{A_i} = \sum -A_i D_{mini}^i \frac{dc}{dl} \tag{10}$$

$A_i$ is a cross-sectional area of a yarn flow, $A_i = 2\pi r L_i$, and $$\frac{dc}{dl}$$

is a concentration gradient in a direction of the gas flow. The gaseous diffusion in the pores in the RVE model obeys Fick's law, and the amount of the gaseous diffusion is set forth below as Equation (11):

$$\frac{dm_2}{dt} = -A_{pore} D_F \frac{dc}{dl} \tag{11}$$

$A_{pore}$ is a cross-sectional area of the pore perpendicular to the direction of the gas flow, and is converted by porosity. $D_F$ is a Fick diffusion coefficient.

According to a cross-sectional area A of the RVE model perpendicular to a diffusion direction, an amount of the gas flow is averaged, and a gaseous diffusion flux in RVE is set forth below as Equation (12):

$$N_A = \frac{dm}{Adt} = -\frac{\left(\sum A_i D_{mini}^i + A_{pore} D_F\right)}{A} \frac{dc}{dl} \tag{12}$$

The equivalent diffusion coefficient of the RVE model in each element of the adjustment sheet is calculated as Equation (13) below:

$$D_{eff} = -\frac{N_A}{\frac{dc}{dl}} = \frac{\left(\sum A_i D_{mini}^i + A_{pore} D_F\right)}{A} \tag{13}$$

Figure 3:
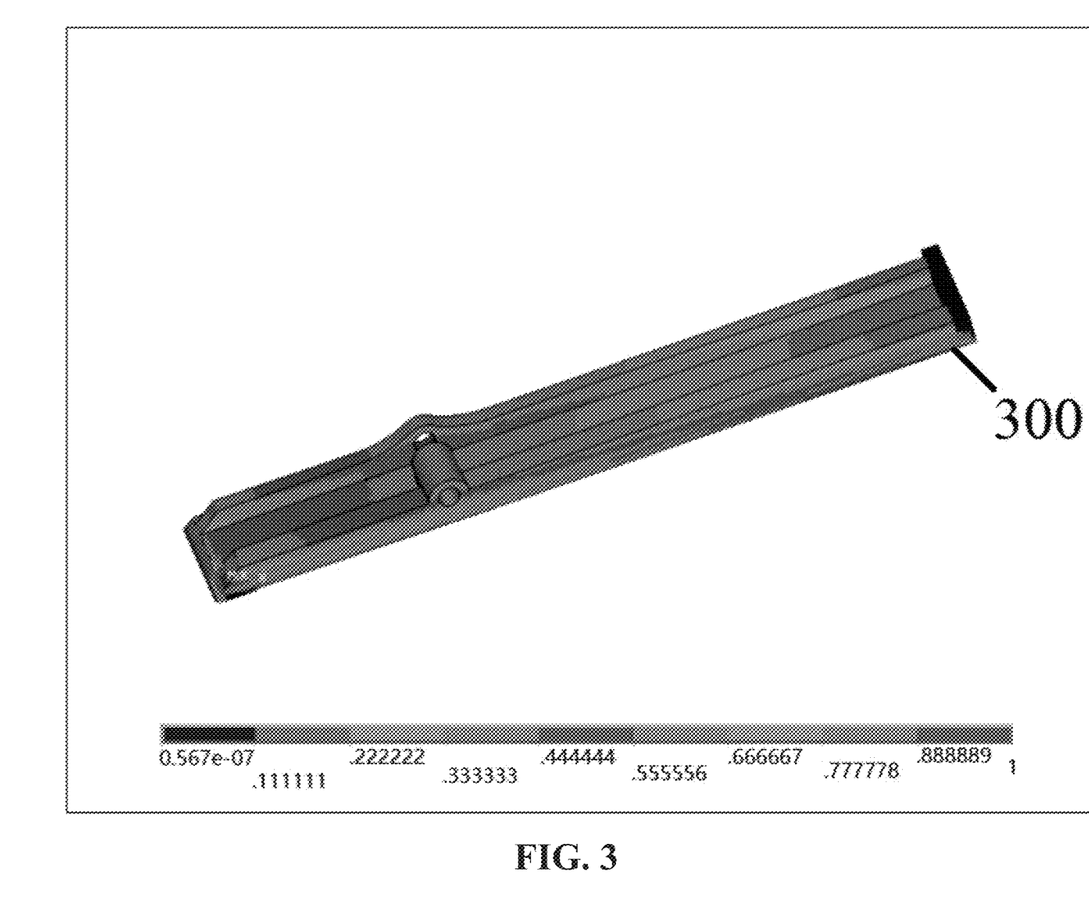
FIG. 3 shows a distribution of equivalent diffusion coefficients in a CMC structural member at an initial stage of oxidation, according to an embodiment.

FIG. 3 is a diagram illustrating a distribution of equivalent diffusion coefficients in a CMC structural member 300 at an initial stage of oxidation, according to an embodiment.

In step 106, the distribution of the gas concentration in the adjustment sheet is then solved. It may be assumed that the same unit is regarded as a homogeneous material, the conditional parameters are equal, there is no internal diffusion phenomenon, and the diffusion only occurs between adjacent units. In a small time increment (dt=1 s), the gaseous diffusion process is treated as one-dimensional steady-state mass transfer.

A relationship between diffusion and oxidation kinetics in an oxidation process is described by partial differential equations according to the law of conservation of mass, as set forth in Equation (14) below:

$$\frac{\partial}{\partial t}(\varepsilon c_A) = \nabla[\nabla(D_{eff} c_A)] - \varepsilon R_A \tag{14}$$

In the Equation (14), ε is a porosity of the CMCs, $c_A$ is the gas concentration, t is time, $D_{eff}$ is the RVE equivalent diffusion coefficient, and $R_A$ is a reaction rate. The distribution of the gas concentration of each element in the structure in a transfer direction is calculated using a finite difference method.

In step 107, the distribution of an oxidation degree in the adjustment sheet is solved next. According to the calculated gas concentration, from an SiC oxidation kinetic model, in a time increment dt, the amount of $O_2$ passing through $SiO_2$ per unit cross section is dn, resulting in Equation (15) below:

$$\frac{dn}{dt} = -D_{O_2}\frac{dc}{dz} \quad (15)$$

According to a chemical reaction formula and boundary conditions, a growth thickness of an oxide at cracks and pores in each element is calculated as Equation (16) below:

$$Z^2 = \frac{4}{3}\frac{M_{SiO_2}D_{O_2}c_0}{\rho_{SiO_2}}t \quad (16)$$

Figure 4:
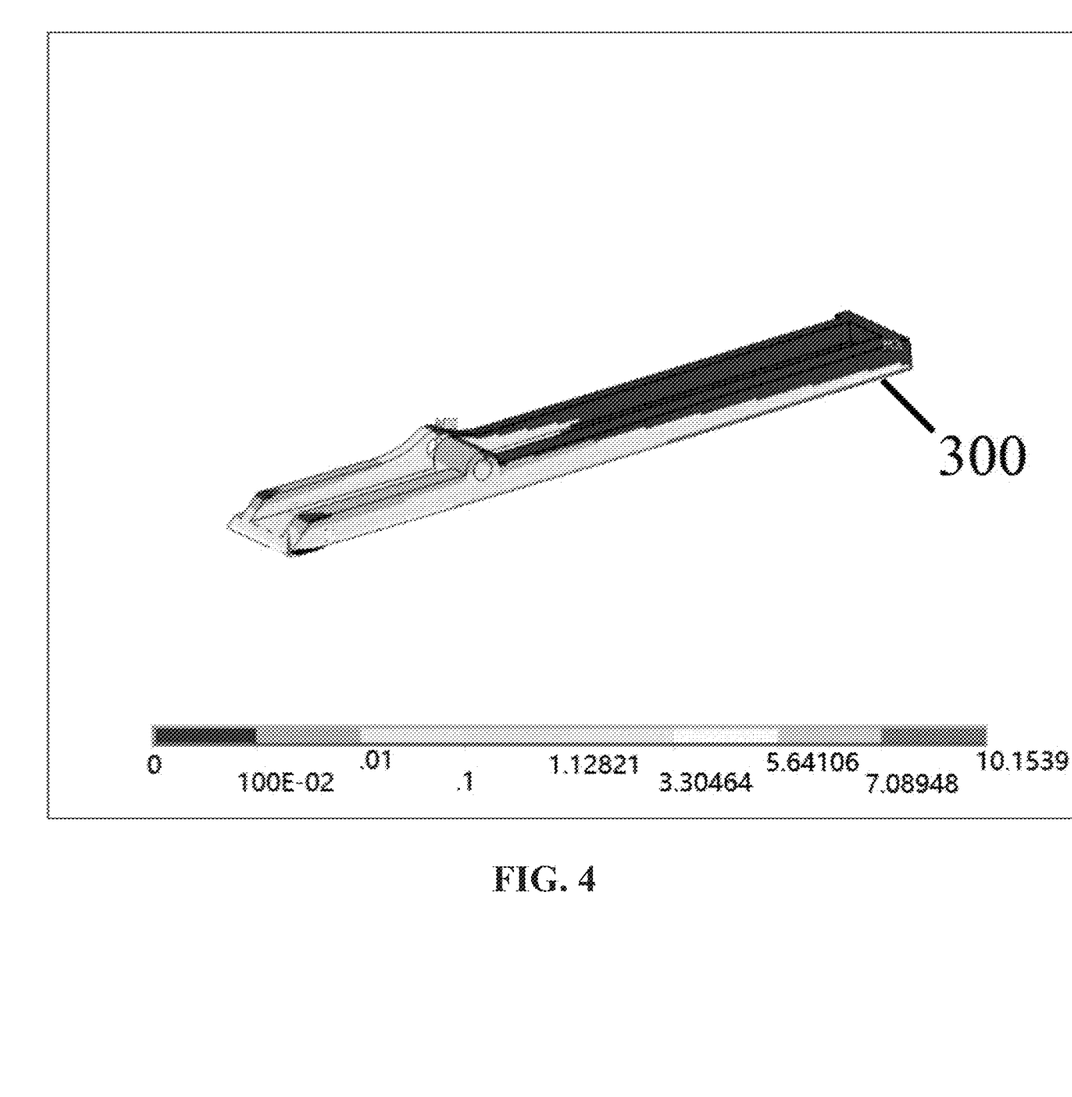
FIG. 4 shows a distribution of thicknesses of oxidation products in the CMC structural member at the initial stage of oxidation, according to an embodiment.

FIG. 4 is a diagram illustrating a distribution of thicknesses with a unit of nm of the oxides at an initial stage of oxidation, according to an embodiment.

In step 108, sealing conditions including changes in the crack width and a pore characteristic quantity of the gas channel are calculated according to the distribution of the thicknesses of the oxides, as set forth in Equation (17) below:

$$d'_{crack} = d_{crack} - 2dz \quad (17)$$

$$\varepsilon' = \varepsilon - \frac{dV}{V_{RVE}}$$

dz represents a change of a material thickness, is a difference between the growth thickness of an oxide layer and a fading thickness of SiC, and is obtained according to a ratio of an oxidation chemical equation, as shown in Equation (18) below:

$$dz = z - z_{SiC} = \left(1 - \frac{\rho_{SiO_2}M_{SiC}}{\rho_{SiC}\rho_{SiO_2}}\right)z \quad (18)$$

$V_{RVE}$ represents a volume of the RVE model, and dV represents a change of a pore volume, and is related to the thickness of the oxidation product, as set forth in Equation (19) below:

$$dV = 4\pi rL \cdot dz \quad (19)$$

An equivalent radius of the fiber bundle r is equal to 0.36 mm, and a length of the warp yarn is equal to 1.6 mm.

If $d_{crack}'=0$, the crack channel in the element is healed, $D_{mini}{}^i=0$, and the gas diffuses only through the pores in the element. A new gas channel characteristic quantity may be substituted above, a new equivalent diffusion coefficient field is calculated, and steps above may be repeated to realize a calculation of distribution of the oxidation products in the CMC adjustment sheet at different times.

According to the given temperature and load conditions, reaction diffusion simulation of different CMC structural members 300 under different a oxidation time could be conducted to realize the oxidation calculation of the structural members 300.

What is described above is merely an implementation of the present disclosure, the scope of protection of the present disclosure is not limited to the above examples, and all technical solutions following the idea of the present disclosure fall within the scope of protection of the present disclosure. It should be noted that several modifications and adaptations made by those of ordinary skill in the art without departing from the principle of the present disclosure should fall within the scope of protection of the present disclosure.

What is claimed is:

1. A method for calculating gaseous diffusion and oxidation evolution of a ceramic matrix composite (CMC) structure, comprising:
    determining a temperature and a load distribution in a structural member;
    determining a matrix crack distribution in the CMC structure by, according to a temperature field and a stress field, based on a matrix cracking model, calculating a matrix crack density and a matrix crack width related to a temperature and a stress in the CMC structure;
    based on the matrix crack distribution, averaging a total amount of gaseous diffusion in a gas flow channel to establish an equivalent diffusion coefficient model of a fiber bundle composite scale related to the matrix crack distribution based on the matrix crack width and the matrix crack density in fiber bundle composites with an axial length;
    establishing a representative volume element (RVE) model of woven CMCs by conducting image recognition on an X-ray computed tomography (XCT) scan image of a meso-structure of the woven CMCs used in the structural member, describing a warp direction by a cosine function, describing weft yarns in a form of a straight line, and observing to obtain geometric parameters to establish the RVE model;
    establishing an equivalent diffusion coefficient model of a RVE scale to characterize a gas flow of the CMC structure, by, based on pore characteristics, regarding the fiber bundle as a homogeneous material, and substituting the equivalent diffusion coefficient model of the fiber bundle composite scale into the yarn of the RVE model to establish the equivalent diffusion coefficient model of the woven CMCs on the RVE scale;
    calculating a distribution of a gas concentration in the CMC structure by calculating the distribution of the gas concentration of each element in the CMC structure in a transfer direction using a finite difference method;
    calculating a distribution of oxidation products in the structure by calculating a growth thickness of an oxide at cracks and pores in each element according to the gas concentration; and
    calculating sealing conditions comprising changes in the crack width and a pore characteristic quantity of the gas channel, substituting a new gas channel characteristic quantity into the averaging and establishing steps, calculating a new equivalent diffusion coefficient field to realize recalibration of the gas channel, and repeating calculation of the distribution of the gas concentration and the calculation of the distribution of oxidation products to realize a calculation of distribution of the oxidation products in the structural member at different times.

2. The method of claim 1, wherein in determining the matrix crack distribution, the matrix crack density $\rho_{crack}$ is:

$$\rho_{crack} = 1/L = \left[1 - \exp\left(-\left(\frac{\sigma}{b_0}\right)^m\right)\right]/L_{sat}$$

where $\sigma$ represents a stress in the fiber bundle, m and $b_0$ represent a Weibull modulus and a Weibull matrix cracking characteristic strength, respectively, and are determined by fitting a transition section of a tensile test curve; and $L_{sat}$ is a saturated crack spacing, and is observed through a test; and the matrix crack width $d_{crack}$ is:

$$\frac{d_{crack}}{d_0} = \frac{1}{T_0}\left(\frac{1}{E_f V_m(\alpha_m - \alpha_f)}\sigma + \Delta T\right)$$

where $d_0$ is a crack width at a normal temperature, $T_0$ is a temperature or material preparation, $\Delta T$ is a temperature difference between a current temperature and a normal temperature, $E_f$ is a fiber elastic modulus, $V_m$ is a volume content of a matrix in the fiber bundle composites, and $\alpha_m$ and $\alpha_f$ are thermal expansion coefficients of the matrix and a fiber, respectively.

3. The method of claim 1, wherein in averaging the total amount of gaseous diffusion, the equivalent diffusion coefficient model of the fiber bundle composite scale related to the matrix crack distribution is:

$$D_{mini} = -\frac{N_A}{\frac{dc}{dl}} = \rho_{crack} d_{crack} D_{gas}$$

where $N_A$ is a gaseous diffusion flux, $$\frac{dc}{dl}$$

represents a concentration gradient, and $D_{gas}$ is a diffusion coefficient of oxygen in a single crack channel;

wherein the diffusion belongs to mixed diffusion, calculation is conducted according to an empirical formula of Fick diffusion related to a diffusion coefficient $D_F$ and Knudsen diffusion related to a diffusion coefficient $D_K$:

$$D_{gas}^{-1} = D_F^{-1} + D_K^{-1};$$

wherein Fick diffusion is calculated as:

$$D_F = \frac{0.00143 T^{1.75}}{P\overline{M}^{0.5}\left[\left(\sum_v\right)_A^{\frac{1}{3}} + \left(\sum_v\right)_B^{\frac{1}{3}}\right]^2};$$

wherein, in a binary diffusion system ($O_2$—CO), a parameter $\overline{M}$ is calculated by:

$$\overline{M} = \frac{2}{M_A^{-1} + M_B^{-1}}$$

where A and B represent $O_2$ and CO respectively;
wherein Knudsen diffusion is calculated as:

$$D_K = \frac{2}{3}\left(\frac{8R_g T}{\pi M_A}\right)^{0.5} d_{crack};$$

wherein a mathematical relationship between an equivalent diffusion coefficient and the matrix crack distribution of the fiber bundle composites is:

$$D_{mini} = \frac{0.00572\sqrt{2} R_g^{0.5} T^{1.75} \rho_{crack} d_{crack}^2}{4\sqrt{2} P\overline{M}^{0.5}\left[\left(\sum_V\right)_A^{1/3} + \left(\sum_V\right)_B^{1/3}\right]^2 R_g^{0.5} d_{crack} + 0.00429(\pi M_A)^{0.5} T^{1.25}}$$

where T is an ambient temperature with a unit of K, P is ambient pressure with a unit of Pa, $R_g$ is a gas constant with a unit of J/(mol/K), $\Sigma_v$ is a molecular diffusion volume, and $\overline{M}$ is a molar mass of mixed gas.

4. The method of claim 1, wherein, in establishing the equivalent diffusion model, a length of any yarn i is $L_i$, a stress value is $\sigma_i$, the matrix crack width of the yarn is $\rho_{crack}^i$, and the equivalent diffusion coefficient in the yarn is:

$$D_{mini}^i = \rho_{crack}^i d_{crack}^i D_{gas}^i,$$

an amount of the gaseous diffusion in each yarn crack in the RVE model is:

$$\frac{dm_1}{dt} = \sum A_i N_{A_i} = \sum -A_i D_{mini}^i \frac{dc}{dl},$$

where $A_i$ is a cross-sectional area of a yarn flow, $A_i = 2\pi r L_i$, and $$\frac{dc}{dl}$$

is a concentration gradient in a direction of the gas flow;
wherein the gaseous diffusion in the pores in the RVE model obeys Fick's law, and the amount of the gaseous diffusion is:

$$\frac{dm_2}{dt} = -A_{pore} D_F \frac{dc}{dl}$$

where $A_{pore}$ is a cross-sectional area of a pore perpendicular to the direction of the gas flow, and is converted by porosity, and $D_F$ is a Fick diffusion coefficient;
wherein, according to a cross-sectional area A of the RVE model perpendicular to a diffusion direction, an amount of the gas flow is averaged, and a gaseous diffusion flux in RVE is:

$$N_A = \frac{dm}{Adt} = -\frac{\left(\sum A_i D_{mini}^i + A_{pore} D_F\right)}{A}\frac{dc}{dl};$$

wherein the equivalent diffusion coefficient of the RVE model is:

$$D_{eff} = -\frac{N_A}{\frac{dc}{dl}} = \frac{\left(\sum A_i D_{mini}^i + A_{pore} D_F\right)}{A}.$$

5. The method of claim 1, wherein, in calculating the distribution of the gas concentration, a relationship between diffusion and oxidation kinetics in an oxidation process is:

$$\frac{\partial}{\partial t}(\varepsilon c_A) = \nabla[\nabla(D_{\mathit{eff}} c_A)] - \varepsilon R_A$$

where $\varepsilon$ is a porosity of the CMCs, $c_A$ is the gas concentration, t is time, $D_{\mathit{eff}}$ is an RVE equivalent diffusion coefficient, and $R_A$ is a reaction rate.

6. The method of claim 1, wherein, in calculating the distribution of oxidation products, the growth thickness z of the oxide at the cracks and pores in each element is calculated as:

$$z^2 = \frac{4}{3}\frac{M_{SiO_2} D_{O_2} c_0}{\rho_{SiO_2}} t$$

wherein $M_{SiO_2}$ is a molar mass of the $SiO_2$, $\rho_{SiO_2}$ is a density of $SiO_2$, $D_{O_2}$ is a diffusion coefficient of $O_2$ in the $SiO_2$, $c_0$ is an oxygen concentration, and t is an oxidation time.

7. The method of claim 1, wherein, in calculating the sealing conditions, the crack width is:

$$d_{crack}' = d_{crack} - 2dz$$

the change of the pore characteristic quantity is:

$$\varepsilon' = \varepsilon - \frac{dV}{V_{RVE}}$$

where dz represents a change of a material thickness, is a difference between the growth thickness of an oxide layer and a fading thickness of SiC, and is obtained according to a ratio of an oxidation chemical equation:

$$dz = z - z_{SiC} = \left(1 - \frac{\rho_{SiO_2} M_{SiC}}{\rho_{SiC} \rho_{SiO_2}}\right) z$$

where $V_{RVE}$ represents a volume of the RVE model, and dV represents a change of a pore volume, and is related to the thickness of the oxidation product:

$$dV = 4\pi r L \cdot dz$$

where r is an equivalent radius of the fiber bundle, and L is a length of a warp fiber bundle.

\* \* \* \* \*